(12) United States Patent
Igney et al.

(10) Patent No.: US 9,448,205 B2
(45) Date of Patent: Sep. 20, 2016

(54) COIL ARRANGEMENT FOR A MAGNETIC INDUCTION IMPEDANCE MEASUREMENT APPARATUS COMPRISING A PARTLY COMPENSATED MAGNETIC EXCITATION FIELD IN THE DETECTION COIL

(75) Inventors: Claudia Hannelore Igney, Erlangen (DE); Francisco Javier Rosell Ferrer, Barcelona (ES); Matthias Hamsch, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 516 days.

(21) Appl. No.: 13/983,873

(22) PCT Filed: Feb. 9, 2012

(86) PCT No.: PCT/IB2012/050578
§ 371 (c)(1),
(2), (4) Date: Aug. 6, 2013

(87) PCT Pub. No.: WO2012/110920
PCT Pub. Date: Aug. 23, 2012

(65) Prior Publication Data
US 2013/0314081 A1    Nov. 28, 2013

(30) Foreign Application Priority Data
Feb. 14, 2011   (EP) .................................. 11154293

(51) Int. Cl.
*G01N 27/90*    (2006.01)
*G01N 27/72*    (2006.01)
(Continued)

(52) U.S. Cl.
CPC ............ *G01N 27/72* (2013.01); *G01N 27/023* (2013.01); *G01V 3/107* (2013.01); *A61B 5/0535* (2013.01); *A61B 2562/0223* (2013.01)

(58) Field of Classification Search
CPC .......... G01R 33/3628; G01R 33/3815; G01R 33/3873
USPC ......................... 324/318, 322, 239, 537, 654
See application file for complete search history.

(56) References Cited

U.S. PATENT DOCUMENTS

| | | |
|---|---|---|
| 5,189,366 A | 2/1993 | Mayo |
| 2008/0074114 A1 | 3/2008 | Candy |

(Continued)

FOREIGN PATENT DOCUMENTS

| | | |
|---|---|---|
| CN | 1635391 A | 7/2005 |
| EP | 1926424 A2 | 6/2008 |

(Continued)

OTHER PUBLICATIONS

Axel Cordes et al, "Breathing Detection with a Portable Impedance Measurement Systems: First Measurements", 31st Annual International Conf. of the IEEE EMBS, Minn., MN, USA, Sep. 2-6, 2009, pp. 2767-2770.

(Continued)

*Primary Examiner* — Vincent Q Nguyen

(57) ABSTRACT

A coil arrangement for a magnetic induction impedance measurement apparatus includes an excitation coil configured to generate a magnetic excitation field in an object, a shimming coil configured to generate a shimming field, and a detection coil configured to detect a magnetic response field generated in response to the magnetic excitation field inducing a current in the object. In order to enhance an accuracy of a determination of a parameter of an object, a value of a field strength of a net magnetic excitation field in the detection coil, being the sum of the excitation field and the shimming field, is approximately within a magnitude range of an average value of a field strength of the magnetic response field in the detection coil.

18 Claims, 3 Drawing Sheets

(51) Int. Cl.
  *G01N 27/02* (2006.01)
  *G01V 3/10* (2006.01)
  *A61B 5/053* (2006.01)

(56) References Cited

U.S. PATENT DOCUMENTS

2008/0246472 A1* 10/2008 Igney .................... A61B 5/053
 324/239
2008/0258717 A1 10/2008 Igney

FOREIGN PATENT DOCUMENTS

WO 2009144461 A2 12/2009
WO 2010052609 A2 5/2010

OTHER PUBLICATIONS

Doga Gursoy et al, "Optimum Receiver Array Design for Magnetic Induction Tomography", Uni Graz, SpezialForschungsBereich F32, Medical University of Graz, SFB-Report No. 2008-010, Sep. 2008, pp. 1-17.

Rosalyn Margaret Seeton, "Sensitivity of Single Coil Electromagnetic Sensors for Breathing Measurements", A thesis submitted to the Faculty of Graduate Studies and Research, Ottawa-Carleton Institute for Biomedical Engineering, Department of Systems and Computer Engineering, Carleton University, Ottawa, Ontario, Canada, Dec. 2008.

S. Watson et al, "A primary field compensation scheme for planar array magnetic induction tomography"; Physiol. Meas. 25 (2004) pp. 271-279.

Olaf Such, On-Body Sensors for Personal Healthcare, Advances in Health Care Technology Care Shaping the Future of Medical, Philips Research, 2006, vol. 6, 6, pp. 463-488.

F. Liebold et al, "Contact-less human vital sign monitoring with a 12 channel synchronous parallel processing magnetic impedance measurement system", 4th European Conference of the International Federation for Medical Engineering Nov. 23-27, 2008, Antwerp, Belgium, vol. 2, pp. 1070-1073.

Igney, C.H. et al "Planar Magnetic Induction Impedance Measurement System with Normal Sensor Alignment for Vital Signs Detection", Research Laboratories, Medical Signal Processing, Weisshausstrasse 2, D-52066 Aachen, Germany. 2005.

* cited by examiner

COIL ARRANGEMENT FOR A MAGNETIC INDUCTION IMPEDANCE MEASUREMENT APPARATUS COMPRISING A PARTLY COMPENSATED MAGNETIC EXCITATION FIELD IN THE DETECTION COIL

CROSS-REFERENCE TO PRIOR APPLICATIONS

This application is the U.S. National Phase application under 35 U.S.C. §371 of International Application No. PCT/IB/2012/050578, filed on Feb. 2, 2012, which claims the benefit of European Patent Application No. 1154293.2, filed on Feb. 14, 2011. These applications are hereby incorporated by reference herein.

FIELD OF THE INVENTION

The invention relates to the field of a magnetic induction impedance measurement technique, and in particular to a coil arrangement for a magnetic induction impedance measurement apparatus, a magnetic induction impedance measurement apparatus for determining a parameter of an object, a method of determining a parameter of an object, and a program element.

BACKGROUND OF THE INVENTION

Magnetic induction impedance measurements represent an non-invasive and contactless examining technique for examining an electrically conductive object. In particular, this technique is suitable for determining a parameter of the object, for example, a physiological characteristic of a person.

Conventionally, a coil arrangement of a magnetic induction impedance measurement apparatus comprises an excitation coil and one or more detection coils. The excitation coil is configured for generating a magnetic excitation field and the one or more detections coils are configured for detecting a magnetic response field generated in response to the magnetic excitation field inducing eddy currents in the object.

In operation of the magnetic induction impedance measurement apparatus, a time-varying current is induced in the excitation coil such that the excitation coil generates the magnetic excitation field which penetrates through the object to be examined and accordingly induces the eddy currents within the object. The magnitude of the eddy currents is based on the magnetic flux density of the magnetic excitation field and the conductivity of the object. The magnetic response field is generated by the flow of the eddy currents in the object and is detected by the one or more detection coils in that a current or a voltage is induced in the one or more detection coils. The induced current or voltage is a measure for the electrical conductivity of the object and depends on the conductivity and the geometry of the object and the geometry of the excitation coil and of the one or more detection coils.

Usually, the excitation coil is located in the vicinity of the one or more detection coils such that the magnetic excitation field is present in the one or more detection coils and accordingly causes an additional current or an additional voltage to be induced in the one or more detection coils. Further, a field strength of the magnetic excitation field in the one or more detection coils is orders of magnitude higher compared to a field strength of the magnetic response field in the one or more detection coils, thereby leading to a poor signal to noise ratio for the detection of the magnetic response field.

When determining the parameter of the object, a signal change which is caused from the parameter of the object in the one or more detection coils may comprise a low value in comparison to a signal value of an average signal caused by the object itself in the one or more detection coils. Consequently, it may be difficult to accurately determine the parameter of the object owing to the presence of the magnetic excitation field in the one or more detection coils and/or the low signal change value of the signal change caused by the parameter of the object.

It is known that the magnetic excitation field in the one or more detection coils may be compensated, in order to increase the accuracy of the determination of the parameter of the object.

WO 2010/052609 A1 describes a coil arrangement for a magnetic induction tomography system. The coil arrangement comprises at least one excitation coil and at least one detection coil. A field strength of the magnetic excitation field in the at least one detection coil is fully compensated or cancelled such that a signal caused by the magnetic response field in the at least one detection coil is usable for calculating a conductivity distribution of the object to be examined and for visualizing the conductivity distribution of the object.

EP 1 926 424 A2 describes a system and a method for inductively measuring a bio-impedance of a conductive tissue. The system comprises an excitation coil and a detection coil with an axis of the detection coil being oriented substantially perpendicular to flux lines of the magnetic excitation field passing through the detection coil. Further, the system comprises a shimming coil configured for generating a magnetic shimming field such that the magnetic excitation field in the detection coil is cancelled.

There may be still a need for determining a parameter of an object with a high accuracy.

SUMMARY OF THE INVENTION

It is an object of the invention to provide a coil arrangement for a magnetic induction impedance measurement apparatus and a respective method which allow for an easy and accurate determination of a parameter of an object.

The object defined above is solved by a coil arrangement for a magnetic induction impedance measurement apparatus, a magnetic induction impedance measurement apparatus for determining a parameter of an object, a method of determining a parameter of an object, and a program element according to the independent claims.

According to an exemplary aspect of the invention, a coil arrangement for a magnetic induction impedance measurement apparatus is provided, the coil arrangement comprising an excitation coil configured for generating a magnetic excitation field in an object, and a detection coil configured for detecting a magnetic response field generated in response to the magnetic excitation field inducing a current in the object, wherein a value of a field strength of a net magnetic excitation field in the detection coil comprises a magnitude range of an average value of a field strength of the magnetic response field in the detection coil.

According to another exemplary aspect of the invention, a magnetic induction impedance measurement apparatus for determining a parameter of an object is provided, the magnetic induction impedance measurement apparatus comprising a coil arrangement as described above, and a parameter determination unit configured for determining the parameter of the object based on the magnetic response field and the magnetic excitation field.

According to another exemplary aspect of the invention, a method of determining a parameter of an object is provided, the method comprising generating by an excitation coil a magnetic excitation field in an object, detecting by a detection coil a magnetic response field in the detection coil, wherein the magnetic response field is generated in response to the magnetic excitation field inducing a current in the object, wherein a value of a field strength of a net magnetic excitation field in the detection coil comprises a magnitude range of an average value of a field strength of the magnetic response field in the detection coil, and determining the parameter of the object based on the magnetic response field and the magnetic excitation field.

A use of a magnetic induction impedance measurement apparatus as described above for determining a parameter of an object is provided.

According to another exemplary aspect of the invention, a program element is provided, which program element, when being executed by a processor, is configured to carry out or control a method of determining a parameter of an object as described above.

A computer-readable medium is provided, in which a computer program for determining a parameter of an object is stored, which computer program, when being executed by a processor, is configured to carry out or control a method of determining a parameter of an object as described above.

In the context of the present application, the term "magnetic field" may particularly denote a magnetic flux density B measured in units of Tesla T and/or a magnetic field intensity H measured in units of Ampere per meter A/m. For ease of reading, the term "magnetic field" may be used in the context of the present application to refer to the magnetic flux density and/or the magnetic field intensity.

The term "net magnetic excitation field in the detection coil" may particularly denote a resulting magnetic excitation field in the detection coil which may be generated by the magnetic excitation field penetrating through the detection coil with one or more different orientations, wherein the magnetic excitation field may be superimposed by another magnetic field, particularly by a magnetic shimming field, penetrating through the detection coil with one or more different orientations.

The term "field strength" of a magnetic field may particularly denote a magnitude of the magnetic field. In particular, the field strength may particularly denote a (signed) value of an amplitude of the magnetic field.

The term "average value of the field strength of the magnetic response field" may particularly denote a timely averaged value of the field strength of the magnetic response field caused by the object. In particular, the average value may be associated with the object being parameter-free.

According to the exemplary aspects of the invention, a determination of a parameter of an object may be based on utilizing a coil arrangement for a magnetic induction impedance measurement apparatus which may provide a partially compensated magnetic excitation field in the detection coil of the coil arrangement. This kind of the determination of the parameter of the object may be based on a recognition that a signal based on the detected magnetic response field and the magnetic excitation field may be sensitive to signal changes caused by the parameter of the object to be determined. In particular, the signal based on the magnetic response field and the magnetic excitation field may show a high sensitivity to small signal changes caused by the parameter of the object if the value of the field strength of the net magnetic excitation field in the detection coil may comprise a magnitude range of the average value of the field strength of the magnetic response field in the detection coil. The latter detection or measurement condition may result in a phase angle (value) between the magnetic excitation field and the magnetic response field being suitable for the determination of the signal change of the magnetic response field in relation to the magnetic excitation field caused by the parameter of the object to be determined. Here, the term "phase angle" may particularly denote an angle between the magnetic excitation field and the magnetic response field, and may be defined as an arc tangents of a ratio between a value of the field strength of the magnetic excitation field and a value of the field strength of the magnetic response field.

In particular, when using the particular detection condition, signal changes caused by the parameter of the object may be accurately determinable, thereby increasing the accuracy of the determination of the parameter of the object.

In particular, since the determination may be based on the detected magnetic response field and the magnetic excitation field, easily accessible measurands may be employable for the determination of the parameter of the object. Thus, the determination of the parameter of the object may be easily executable.

Next, further exemplary embodiments of the coil arrangement for a magnetic induction impedance measurement apparatus will be explained. However, these embodiments also apply to the magnetic induction impedance measurement apparatus, the method of determining a parameter of an object, the use of the magnetic induction impedance measurement apparatus for determining a parameter of an object, the program element, and the computer-readable medium.

In particular, the value of the field strength of the magnetic excitation field in the detection coil may be (approximately) within a magnitude range of 20 percent, particularly 10 percent, further particularly 5 percent, of the average value of the field strength of the magnetic response field in the detection coil. Thus, the sensitivity of the coil arrangement for the signal change caused by the parameter of the object and accordingly the accuracy of the determination of the parameter of the object may be further increased, since these percentage ranges may correspond to a better signal to noise ratio of the signal change caused by the parameter of the object.

The value of the field strength of the magnetic excitation field in the detection coil may be (approximately) equal to the average value of the field strength of the magnetic response field in the detection coil. Accordingly, a phase angle value between the magnetic excitation field and the magnetic response field may be (about) 45°. This measurement condition may correspond to the coil arrangement showing an optimum sensitivity for the signal associated with the parameter of the object, whereby the accuracy of the determination of the parameter of the object may be further enhanced.

The coil arrangement may further comprise a shimming coil configured for generating a magnetic shimming field in the detection coil such that the value of the field strength of the net magnetic excitation field in the detection coil may comprise the magnitude range of the average value of the field strength of the magnetic response field in the detection coil. This conventional measure may allow for a superposition of the magnetic excitation field and the magnetic shimming field in the detection coil such that the value of the field strength of the net magnetic excitation field in the detection coil may be adjustable to the desired value for the determination of the parameter of the object.

The coil arrangement may further comprise at least another detection coil (or a plurality of detection coils) configured for detecting the magnetic response field generated in response to the magnetic excitation field inducing the current in the object, and a value of a field strength of a net magnetic excitation field in the at least another detection coil (or in the plurality of detection coils) may comprise a magnitude range of an average value of a field strength of the magnetic response field in the at least another detection coil (or in the plurality of detection coils). In particular, the value of the field strength of the net magnetic excitation field in the detection coil and the value of the field strength of the net magnetic excitation field in the at least another detection coil may be identical or may be different to one another. Accordingly, the average value of the field strength of the magnetic response field in the detection coil and the average value of the field strength of the magnetic response field in the at least another detection coil may be identical or may be different to one another. Thus, by providing the coil arrangement with at least two detection coils, a spatial resolution of the object may be provided, thereby turning the coil arrangement usable for tomography applications.

The coil arrangement may comprise a planar configuration. Here, the term "planar" coil arrangement may particularly denote a coil configuration in which components thereof (particularly the excitation coil and the detection coil) may (essentially) extend in a common plane or in planes being (approximately) parallel to one another but (closely) spaced from one another. In particular, the detection coil and at least another detection coil may comprise a planar gradiometer configuration in which the detection coil and the at least another detection coil may be placed in a common plane equidistant from the excitation coil. Here, the at least another detection coil may correspond to the above described at least another detection coil configured for detecting the magnetic response field. In particular, the coil arrangement may comprise a planar orthogonal configuration in which the excitation coil and at least one of the detection coil and at least another detection coil may be arranged in a common plane, and in which at least one of the detection coil and the at least another detection coil may be aligned along magnetic flux lines of the magnetic excitation field. Here, the at least another detection coil may correspond to the above described at least another detection coil configured for detecting the magnetic response field.

In particular, alternatively, the coil arrangement may comprise an axial gradiometer configuration in which the detection coil and at least another detection coil may be placed equidistantly from the excitation coil along a common axis of the detection coil and the at least another detection coil. Here, the at least another detection coil may correspond to the above described at least another detection coil configured for detecting the magnetic response field. The detection coil and the another detection coil are connected oppositely and in series to one another such that the net magnetic excitation field in the detection coil may be adjusted to a desired value.

Next, further exemplary embodiments of the magnetic induction impedance measurement apparatus will be explained. However, these embodiments also apply to the coil arrangement, the method of determining a parameter of an object, the use of the magnetic induction impedance measurement apparatus for determining a parameter of an object, the program element, and the computer-readable medium.

The magnetic induction impedance measurement apparatus may further comprise a phase difference value determination unit configured for determining a phase difference value between a phase value of a phase of the magnetic excitation field and a phase value of a phase of the magnetic response field, and the parameter determination unit may be configured for determining the parameter of the object based on the determined phase difference value. The term "phase" of a magnetic field may particularly denote an offset of a frequency of the magnetic field (multiplied by a time). In particular, as the detected magnetic response field may comprise a phase value being a superposition of the phase value of the magnetic excitation field, the phase value of the magnetic response field caused by the object, and the phase value of the magnetic response field caused by the parameter of the object, the phase difference value may be indicative of the parameter of the object. Thus, the determination of the parameter of the object may rely on a simple mathematical evaluation.

In particular, the phase difference determination unit may be configured for determining a phase value of the magnetic response field and/or may be configured for operating on the phase value of the magnetic response field.

In particular, the phase difference determination unit may be configured for repeatedly determining the phase difference value between the phase value of the phase of the magnetic excitation field and the phase value of the phase of the magnetic response field over a time period such that a time evolution or time dependency of the phase difference may be utilized for the determination of the parameter of the object. Thus, a time-dependent parameter of the object may be determinable. Further, using a time information of the parameter of the object may increase the accuracy of the determination of the parameter of the object.

In particular, the phase difference determination unit may be configured for operating on at least two or all signals indicative of the magnetic response fields in at least two detection coils or in all detection coils.

In particular, the magnetic induction impedance measurement apparatus may comprise a (separate) phase difference determination unit as described above for each detection coil of the coil arrangement.

In particular, the parameter determination unit may be configured for comparing the determined phase difference value(s) to a reference phase difference value associated with the object being parameter-free. In particular, the comparing may comprise subtracting the reference phase difference value from (each of) the determined phase difference value(s). In particular, the parameter determination unit may be configured for generating the reference phase value and storing the reference phase value for the determination of the parameter of the object.

In particular, the parameter determination unit may comprise a high pass filter configured for filtering the determined (time-dependent) phase difference value(s) particularly by applying a threshold value (as the reference phase difference value) to the (time-dependent) determined phase difference value(s) such that only the signal change(s) associated with the parameter of the object may pass the high-pass filter for a further determination of the parameter of the object.

The magnetic induction impedance measurement apparatus may further comprise an excitation field phase value generating unit configured for generating a excitation phase value signal indicative of a phase value of the phase of the magnetic excitation field and to be provided to the excitation coil and the phase difference value determination unit. This measure may cause the phase difference value determination unit to be provided with the actual phase of the magnetic excitation field in an easy way, thereby increasing the accuracy of the determination of the parameter of the object.

The magnetic induction impedance apparatus may be configured as a magnetic induction impedance tomography apparatus, thereby being usable for providing spatially dependent information of the parameter of the object. In particular, the determination of the parameter of the object may be based on sectional images of the object generated based on the phase difference values.

In particular, the object may be a person, and the parameter may comprise a physiological parameter of the person. In particular, the physiological parameter may comprise a vital sign such as at least one of a lung activity, a heart activity, and a brain activity. In particular, the magnetic induction impedance apparatus may be usable for clinical applications, for example for neonatal applications when determining a respiration or respiratory rate of newborn baby, or in the automotive industry, for example, for determining drowsiness of a driver. In the latter application, the magnetic induction impedance apparatus may be integrated in a car seat of the driver, in order to determine the respiration or respiratory rate of the car driver.

In particular, at least two of the described units of the magnetic induction impedance measurement apparatus may be combined to form one unit.

In particular, each of the above described units comprising multiple functionalities may be embodied as separate units each of which comprising only one of the multiple functionalities.

Next, further exemplary embodiments of the method of determining the parameter of the object will be explained. However, these embodiments also apply to the coil arrangement, the magnetic induction impedance measurement apparatus for determining a parameter of an object, the use of the magnetic induction impedance measurement apparatus for determining a parameter of an object, the program element, and the computer-readable medium.

The method may further comprise adjusting the value of the field strength of the net magnetic excitation field in the detection coil (and optionally in the at least another detection coil) prior to the determining of the parameter of the object. Thus, the determination of the parameter of the object may be executed at such a detecting condition which may comprise an improved sensitivity for a signal change caused by the parameter of the object.

The adjusting may comprise at least one of adjusting a shape of the excitation coil and/or the detection coil (and/or an at least another detection coil), adjusting a relative arrangement of the excitation coil and the detection coil (and/or the at least another detection coil), adjusting a shape of a shimming coil, and adjusting a relative arrangement of the shimming coil and at least one of the excitation coil and the detection coil (and/or the at least another detection coil). These measures may represent easily (particularly electronically) adjustable parameters impacting the value of the field strength of the net magnetic excitation field in the detection coil and/or in the at least another detection coil.

The adjusting may comprise at least one of arranging a reference object in a vicinity of the excitation coil and the detection coil, and at least one of detecting and calculating (particularly using simulations) the magnetic response field, and arranging the object in a vicinity of the excitation coil and the detection coil, and detecting the magnetic response field over a time period associated with the field strength of the magnetic response field comprising the average value. Thus, in the first option the value of the field strength of the net magnetic excitation field in the detection coil may be adjusted by using a reference object which may not exhibit the parameter to be determined. The second option may utilize the fact that the parameter of the object may exhibit a timely periodic evolution such that the average value of the magnetic response field may be associated with the signal contribution of the magnetic response field caused by the parameter of the object being averaged out.

BRIEF DESCRIPTION OF THE DRAWINGS

These and other aspects of the invention will be apparent from and elucidated with reference to the embodiments described hereinafter.

DETAILED DESCRIPTION OF EMBODIMENTS

Figure 1:
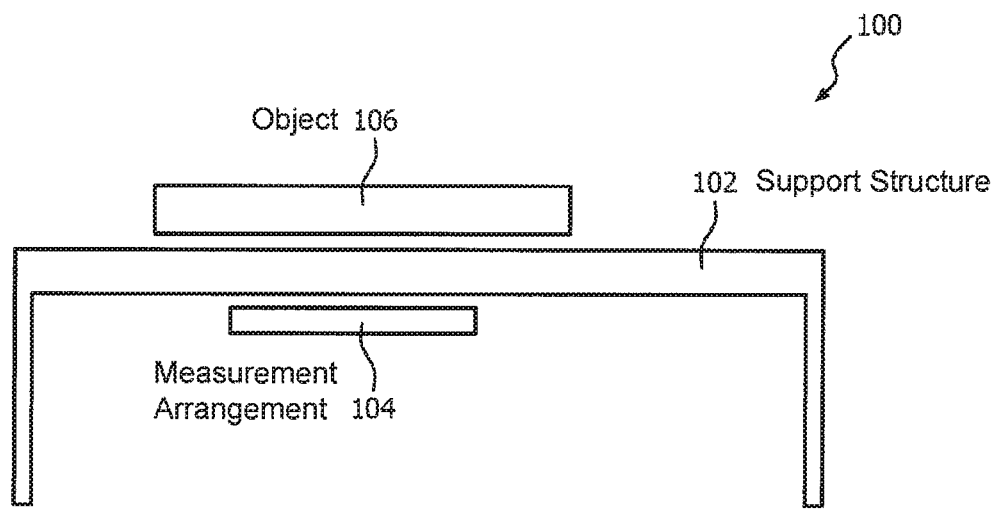
FIG. 1 shows a magnetic induction impedance measurement apparatus for determining a respiratory rate of a person according to an exemplary embodiment of the invention.

The illustration in the drawing is schematic. It is noted that in different figures, similar or identical elements are provided with the same reference signs or with reference signs, which are different from the respective reference signs only within a first digit.

Referring to FIG. 1, a magnetic induction impedance measurement apparatus 100 for determining a respiratory rate of a person according to an exemplary embodiment of the invention will be explained. The apparatus 100 is configured for executing the respiratory rate based on an evaluation of a time dependency of a phase difference between the magnetic excitation field and a detected magnetic response field at a detection condition corresponding to a phase angle of 45 degrees between the net magnetic excitation field in detection coils and the detected magnetic response field.

The apparatus 100 comprises a support structure 102 in the form of a bed. A measurement arrangement 104 is fixed below a lying surface of the support structure 102. A person 106 to be examined is placeable on the lying surface of the support structure 102 in the region of the measurement arrangement 104.

Figure 2:
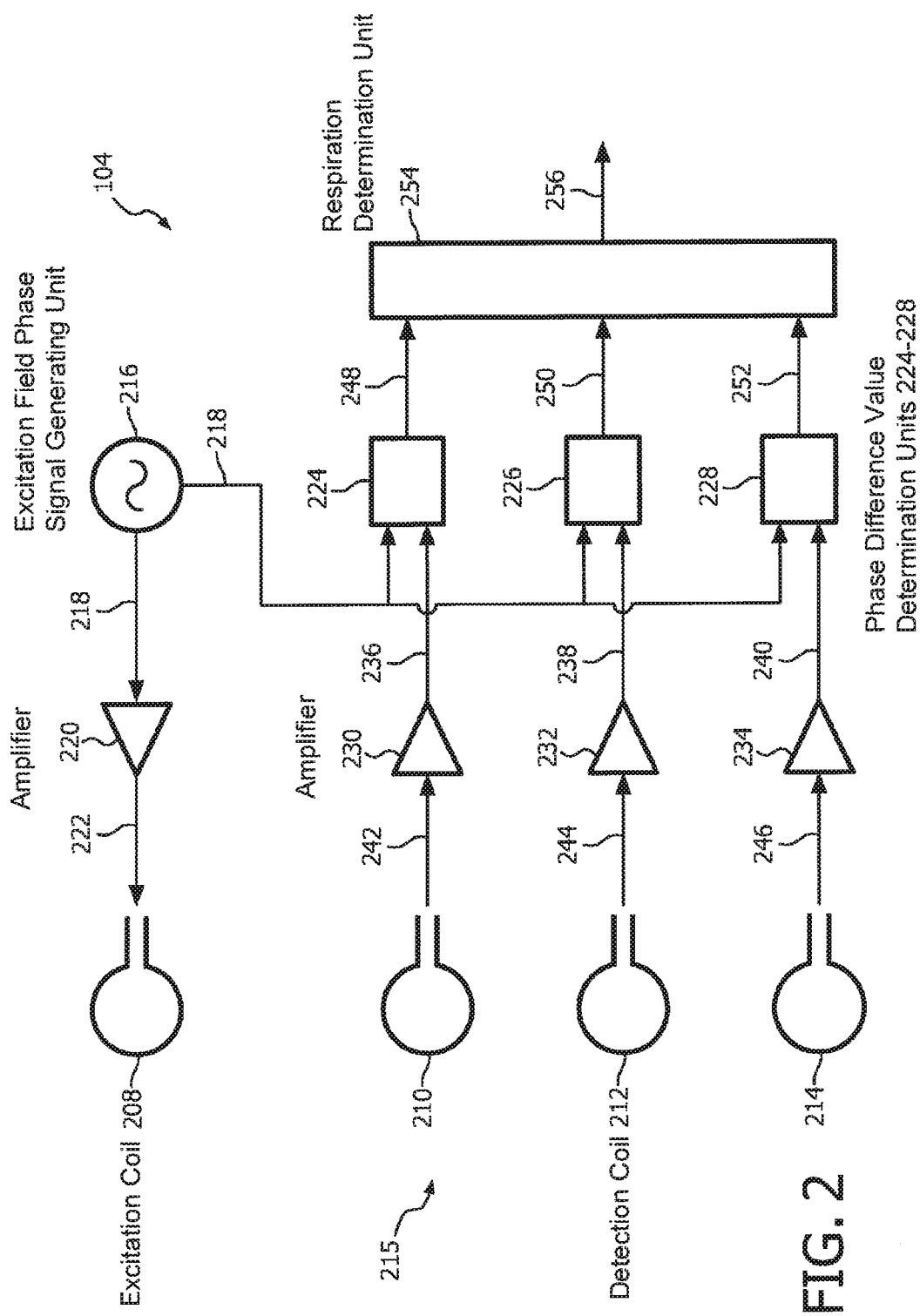
FIG. 2 shows a measurement arrangement of the magnetic induction impedance measurement apparatus in FIG. 1.

Referring to FIG. 2, the measurement arrangement 104 will be explained in more detail. The measurement arrangement 104 comprises an excitation coil 208 configured for generating a magnetic excitation field in a body region of interest of the person 106 and three detection coils 210-214 each of which being configured for detecting a magnetic response field generated in response to the magnetic excitation field inducing eddy currents in the body region of the person 106. The excitation coil 208 and the detection coils 210-214 form a coil arrangement 215 which will be described in more detail with reference to FIG. 3.

An excitation field phase value generating unit 216 is configured for generating an excitation phase value signal 218 indicative of a phase value of a phase of the magnetic excitation field. The excitation phase value signal 218 is to be provided to the excitation coil 208 via an amplifying unit 220. Accordingly, the amplifying unit 220 is configured for outputting an amplified excitation phase value signal 222.

The measurement arrangement 104 further comprises three phase difference value determination units 224-228 each of which being configured for determining a respective phase difference value between a phase of the magnetic excitation field and a phase of the magnetic response field detected by the respective detection coil 210-214. To this end, each of the phase difference value determination units 224-228 is connected to the respective detection coil 210-214 via an amplifying unit 230-234. Each of the phase difference value determination units 224-228 is configured for operating on the excitation phase signal 218 and an amplified magnetic response field signal 236-240 outputted by the amplifying unit 230-234. Accordingly, each of the amplifying units 230-234 is configured for amplifying an inputted magnetic response field signal 242-246 generated by the respective detection coils 210-214 when detecting the magnetic respective response field in the detection coil 210-214.

A respiration determination unit 254 is configured for operating on inputted phase difference value signals 248-252 outputted by the phase difference value determination units 224-228. To this end, the respiration determining unit 254 is configured for subtracting a phase difference reference value associated with the person 106 not respiring from the determined phase difference values associated with the phase difference value signals 248-252. An output signal 256 outputted by the respiration determination unit 254 is indicative of the respiration state or act of the person 106 and is to be used for a further evaluation of the respiratory rate of the person 106 to be examined.

The excitation field phase signal generating unit 216 is configured as a signal generator being controlled by a reference oscillator. The amplifying unit 220 is configured as a power amplifier, and the amplifying units 230-234 are configured as low noise amplifiers. The phase difference value determination units 224-228 are configured as phase detectors, a and the respiration determining unit 254 is configured as a digital signal processor having an integrated analog-to-digital convertor.

As the detection coils 210-214 are spatially distributed with respect to the body region of the person 106, the signal 256 comprises information about a sectional image of the body region of the person 106 indicating the electrical conductivity of the examined body region of the person 106.

The measurement arrangement 104 is configured for repeatedly determining the respiration of the person 106 over a time period such that the respiratory rate of the person 106 is determinable from the timely dependent signal 256.

Alternatively, the respiration determination unit 254 is configured for determining the respiratory rate of the person 106 by associating the respiration state of the person 106 with a measurement time. Accordingly, the signal 256 is indicative of the respiratory rate of the person 106.

Figure 3:
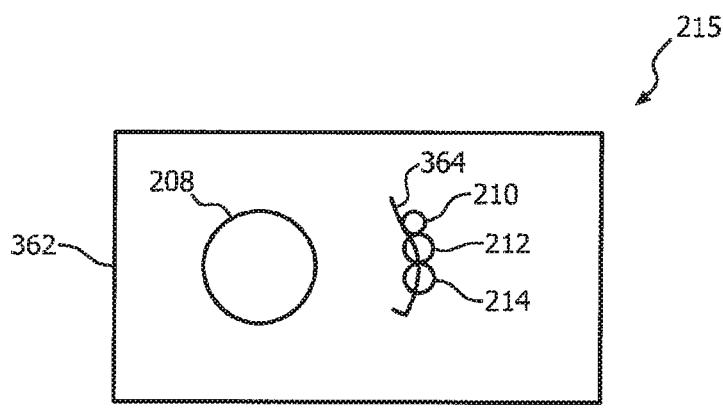
FIG. 3 shows a coil arrangement according to an exemplary embodiment of the invention of the magnetic induction impedance measurement apparatus of FIG. 1.

Referring to FIG. 3, the coil arrangement 215 of the measurement arrangement 104 will be explained in more detail.

The planar coil arrangement 215 comprises a substrate 362 on which the circular excitation coil 208 and the circular detection coils 210-214 are arranged in a movable way. The detection coils 210-214 are arranged along an angular range of the excitation coils 208. Further, the coil arrangement 215 comprises a shimming coil 364 configured as a metal plate and configured for generating a magnetic shimming field in each of the detection coils 210-214 such that a field strength of the net magnetic excitation field in the respective detection coil 210-214 is adjustable to a suitable value. An arrangement and a shape of the excitation coil 208, the detection coils 210-214, and the shimming coil 364 are electronically adjustable by a control unit of the measurement arrangement 104.

In the following, an operation of the apparatus 100 will be explained.

The person 106 is placed on the support structure 102. Further, a value of the field strength of the net magnetic excitation field in the respective detection coil 210-214 is adjusted to be equal to an average value of the magnetic response field detected by each of the detection coils 210-214.

Next, a reference phase difference value signal is generated for the determination of the respiratory rate of the person 106. The excitation phase signal generating unit 216 generates the excitation phase signal 218 which is provided to the magnetic excitation coil 208 and to each of the phase difference determination units 224-228. Each of the detection coils 210-214 detects a magnetic response field and provides the magnetic response field signal 242-246. Respective amplified signals 236-240 are generated by the amplifying units 230-234 based on the inputted magnetic response field signal 242-246, and are supplied to the phase difference value determination units 224-228. Each of the phase difference value determination units 224-228 determines the respective phase difference value and outputs a respective phase difference value signal 248-252 indicative of the phase difference between the phase of the excitation field and the phase of the magnetic response field. Thereupon, the respiration determination unit 254 determines an average value of the phase difference values associated with the phase difference value signals 248-252 and stores this average value as the generated reference phase difference value to be used for the evaluation of the respiratory rate of the person 106.

Next, the respiratory rate of the person 106 is determined. The excitation phase signal generating unit 216 generates the excitation phase signal 218 which is provided to the magnetic excitation coil 208 and to each of the phase difference determination units 224-228. Each of the detection coils 210-214 detects a magnetic response field and provides the magnetic response field signal 242-246. Respective amplified signals 236-240 are generated by the amplifying units 230-234 based on the inputted magnetic response field signal 242-246, and are supplied to the phase difference value determination units 224-228. Each of the phase difference value determination units 224-228 determines the respective phase difference value and outputs a respective phase difference value signal 248-252 indicative of the phase difference between the phase of the excitation field and the phase of the magnetic response field. Thereupon, the respiration determination unit 254 subtracts the stored reference phase difference value from the phase difference values associated with the phase difference value signals 248-252 and outputs the respective respiration signal 256 for a further evaluation of the respiratory rate of the person 106.

Alternatively, the respiration determination unit 254 may comprise a high-pass filter which may eliminate static portions of the phase difference value signals 248-252 which may correspond to the signal contribution caused by the body region of the person 106 but not by the respiration of the person 106. Accordingly, the high-pass filter outputs a signal indicative of the signal change of the phase difference value signals 248-252 with respect to a signal caused by the body region of the person 106 when not respiring.

In the following, the adjustment of the value of the field strength of the net magnetic excitation field in the detection coils 210-214 will be explained in more detail. This adjustment procedure is executed prior to the above described determination of the parameter of the person.

In a first option, a reference object is placed on the support structure 102. This reference object is configured as a body region dummy having a suitable material composition similar to the material composition of the body region of the person 106. The shape and the relative arrangement of the excitation coil 208, the detection coils 210-214 and the shimming coil 364 are electronically varied until the respective value of the field strength of the net magnetic excitation field in each of the detection coils 210-214 is equal to the respective average value of the magnetic response field in the detection coils 210-214 measured for the reference object. Alternatively, the respective magnetic response field in the detection coils 210-214 is not measured but simulated using suitable algorithms based on the material composition of the reference object, in order to determine the optimal shapes and relative arrangements of the excitation coil 208, the detection coils 210-214 and the shimming coil 364 for the above mentioned measurement condition.

In a second option, the person 106 to be examined is placed on the support structure 102 of the apparatus 100, and the magnetic response field is detected in the detection coils 210-214 over a sufficiently long time period such that a signal change caused by the respiration of the person 106 is averaged out in the signal 248-252, 256.

Figure 4:
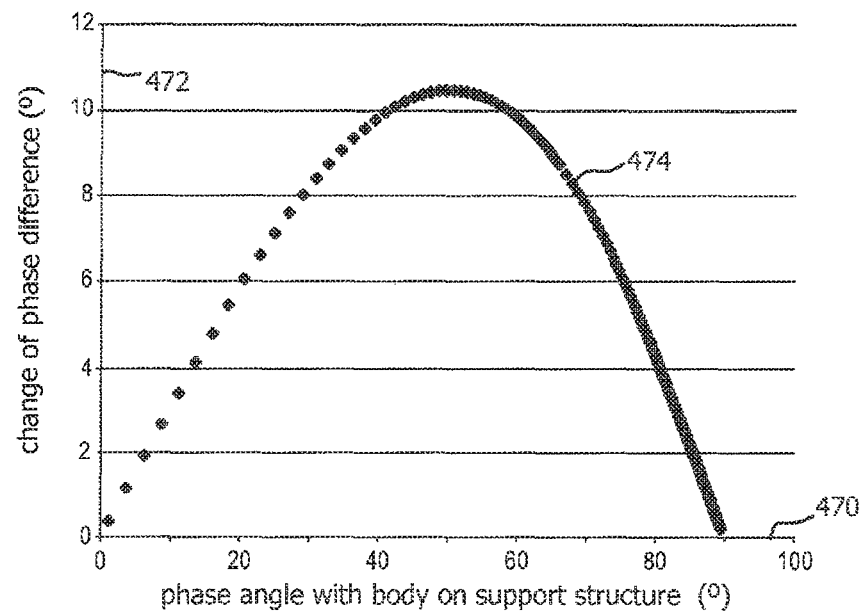
FIG. 4 shows a diagram illustrating a phase angle dependency of a phase difference value determined by the magnetic induction impedance measurement apparatus of FIG. 1 for a person.
Figure 5:
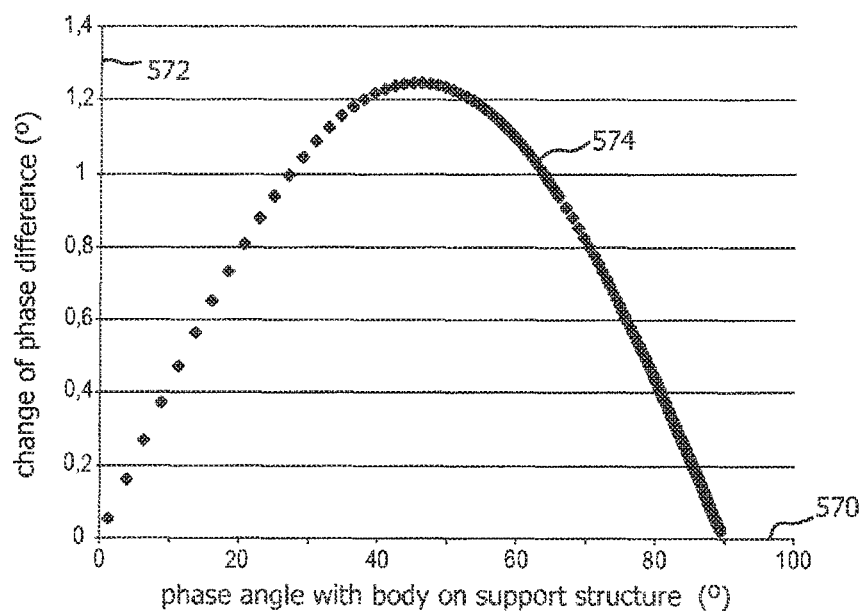
FIG. 5 shows a diagram illustrating phase angle dependency of a phase difference value determined by the magnetic induction impedance measurement apparatus of FIG. 1 for another person.

FIGS. 4 and 5 show diagrams illustrating a phase angle dependency of the phase difference value signal 248 measured for two different persons 106.

An abscissa 470 of the diagram of FIG. 4 corresponds to a phase angle for a detection condition when the person 106 is placed on the support structure 102. An ordinate 472 of the diagram of FIG. 4 corresponds to the phase difference value associated with the signal 248 and being indicative of the respiration of the person 106. A signal curve 474 shows a root-like behavior with a maximum in the range of the phase angle value being equal to 45°. This phase angle value corresponds to the value of the field strength of the net magnetic excitation field in the detection coil 210 being equal to the value of the field strength of the magnetic response field in the detection coils 210. For sake of clarity, it is noted that the phase angle value equal to zero corresponds to a fully compensated (net) magnetic excitation field in the detection coils 210-214, and the phase angle value equal to 90° corresponds to a not compensated (net) magnetic excitation field in the detection coils 210-214 with the signal strength of the net magnetic excitation field in the detection coil 210 being by a factor of 50 larger than the magnetic response field detected by the detection coil 210.

The diagram illustrated in FIG. 5 with abscissa 570 and ordinate 572 is similar to the diagram illustrated in FIG. 4 except that absolute values of the curve 574 are by an order of magnitude lower than the signal values of the curve 474, since the examined another person 106 comprises a lower respiration.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the use of the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A coil arrangement for a magnetic induction impedance measurement apparatus, the coil arrangement comprising:
    an excitation coil configured to generate a magnetic excitation field in an object;
    a detection coil configured to detect a magnetic response field generated in response to the magnetic excitation field inducing a current in the object;
    a shimming coil configured to generate a magnetic shimming field in the detection coil; and
    a control unit configured to adjust the arrangement of the excitation coil, the detection coil and the shimming coil such that the field strength of a net magnetic excitation field in the detection coil resulting from the magnetic excitation field and the magnetic shimming field substantially equals an average value of a field strength of the magnetic response field in the detection coil.

2. The coil arrangement according to claim 1, wherein the value of the field strength of the net magnetic excitation field in the detection coil is within a range of 20% of the average value of the field strength of the magnetic response field in the detection coil.

3. The coil arrangement according to claim 1, further comprising:
    at least another detection coil configured to detect the magnetic response field generated in response to the magnetic excitation field inducing the current in the object, wherein a value of a field strength of a net magnetic excitation field in the at least another detection coil substantially equals or is less than an average value of a field strength of the magnetic response field in the at least another detection coil.

4. The coil arrangement according to claim 1, wherein the coil arrangement comprises a planar configuration.

5. The coil arrangement of claim 1, wherein a phase difference between the net magnetic excitation field in detection coils and the magnetic response field is 45 degrees.

6. The coil arrangement of claim 1, wherein the value of the field strength of the net magnetic excitation field in the detection coil is within a range of 5% of the average value of the field strength of the magnetic response field in the detection coil.

7. A magnetic induction impedance measurement apparatus for determining a parameter of an object, the magnetic induction impedance measurement apparatus comprising:
    a coil arrangement, and
    a parameter determination unit configured to determine the parameter of the object based on a magnetic response field and a magnetic excitation field, wherein the coil arrangement comprises:
    an excitation coil configured to generate the magnetic excitation field in the object;
    a detection coil configured to detect the magnetic response field generated in response to the magnetic excitation field inducing a current in the object;
    a shimming coil configured to generate a magnetic shimming field in the detection coil; and a control unit configured to adjust the arrangement of the excitation coil, the detection coil and the shimming coil such that the field strength of a net magnetic excitation field in the detection coil resulting from the magnetic excitation field and the magnetic shimming field substantially equals an average value of a field strength of the magnetic response field in the detection coil.

8. The magnetic induction impedance measurement apparatus according to claim 7, the magnetic induction impedance measurement apparatus further comprising:
a phase difference value determination unit configured to determine a phase difference value between a phase value of a phase of the magnetic excitation field and a phase value of a phase of the magnetic response field, wherein the parameter determination unit is configured to determine the parameter of the object based on the determined phase difference value.

9. The magnetic induction impedance measurement apparatus according to claim 7, the magnetic induction impedance measurement apparatus further comprising:
an excitation field phase value generating unit configured to generate an excitation phase value signal indicative of a phase value of the phase of the magnetic excitation field and to be provided to the excitation coil and the phase difference value determination unit.

10. The magnetic induction impedance measurement apparatus according to claim 7, wherein the magnetic induction impedance measurement apparatus is configured as a magnetic induction impedance tomography apparatus.

11. The magnetic induction impedance measurement apparatus of claim 7, wherein a phase difference between the net magnetic excitation field in detection coils and the magnetic response field is 45 degrees.

12. A method of determining a parameter of an object, the method comprising acts of:
generating by an excitation coil a magnetic excitation field in an object;
detecting by a detection coil a magnetic response field in the detection coil, wherein the magnetic response field is generated in response to the magnetic excitation field inducing a current in the object;
generating a magnetic shimming field by a shimming coil in the detection coil;
adjusting by a control unit the arrangement of the excitation coil, the detection coil and the shimming coil such that the field strength of a net magnetic excitation field in the detection coil resulting from the magnetic excitation field and the magnetic shimming field substantially equals or is less than an average value of a field strength of the magnetic response field in the detection coil; and
determining the parameter of the object based on the detected magnetic response field and the magnetic excitation field.

13. The method according to claim 12, further comprising an act of:
adjusting the value of the field strength of the net magnetic excitation field in the detection coil prior to the determining of the parameter of the object.

14. The method according to claim 13, wherein the act of adjusting the value comprises at least one of acts of:
adjusting a shape of the excitation coil and/or the detection coil;
adjusting a relative arrangement of the excitation coil and the detection coil;
adjusting a shape of a shimming coil; and
adjusting a relative arrangement of the shimming coil and at least one of the excitation coil and the detection coil.

15. The method according to claim 12, wherein the adjusting act comprises at least one of acts of:
arranging a reference object in a vicinity of the excitation coil and the detection coil, and at least one of detecting and calculating magnetic response field for the reference object; and
arranging the object in a vicinity of the excitation coil and the detection coil, and detecting the magnetic response field over a time period associated with the field strength of the magnetic response field comprising the average value.

16. The method of claim 12, wherein a phase difference between the net magnetic excitation field in detection coils and the magnetic response field is 45 degrees.

17. A non-transitory computer readable medium comprising computer instructions which, when executed by a processor, configure the processor to perform the acts of:
causing an excitation coil to generate a magnetic excitation field in an object;
causing a detection coil to detect a magnetic response field in the detection coil, wherein the magnetic response field is generated in response to the magnetic excitation field inducing a current in the object;
causing a shimming coil to generate a magnetic shimming field in the detection coil;
adjusting the arrangement of the excitation coil, the detection coil and the shimming coil such that the field strength of a net magnetic excitation field in the detection coil resulting from the magnetic excitation field and the magnetic shimming field substantially equals or is less than an average value of a field strength of the magnetic response field in the detection coil; and
determining a parameter of the object based on the detected magnetic response field and the magnetic excitation field.

18. The non-transitory computer readable medium of claim 17, wherein a phase difference between the net magnetic excitation field in detection coils and the magnetic response field is 45 degrees.

* * * * *